United States Patent [19]

Riess

[11] 4,379,694

[45] Apr. 12, 1983

[54] DENTAL IMPLANT

[75] Inventor: Guido Riess, Garmisch-Partenkirchen, Fed. Rep. of Germany

[73] Assignee: Neodontics, Inc., Laguna Niguel, Calif.

[21] Appl. No.: 959,292

[22] Filed: Nov. 9, 1978

[30] Foreign Application Priority Data

Jun. 1, 1978 [DE] Fed. Rep. of Germany ....... 2824118

[51] Int. Cl.³ ............................................. A61C 8/00
[52] U.S. Cl. ...................................... 433/201; 433/173
[58] Field of Search ..................... 32/10 A; 128/92 C; 3/1.9; 106/35; 433/173, 174, 175, 176, 201

[56] References Cited

U.S. PATENT DOCUMENTS

| 3,789,029 | 1/1974 | Hodosh | 32/10 A |
| 3,919,773 | 11/1975 | Freeman | 32/10 A |
| 4,073,999 | 2/1978 | Bryan et al. | 128/92 C |
| 4,121,340 | 10/1978 | Patrick | 32/10 A |
| 4,131,597 | 12/1978 | Blüethgen et al. | 32/10 A |
| 4,178,686 | 12/1979 | Riess et al. | 433/201 |

FOREIGN PATENT DOCUMENTS 2546824 4/1977 Fed. Rep. of Germany ..... 32/10 A
2317904 2/1977 France ............................... 32/10 A

OTHER PUBLICATIONS

"Pilot Studies of a Porous Implant in Dentistry and Oral Surgery", Kent et al., J. Oral Surgery, vol. 30, 8-72, pp. 608-615.

Primary Examiner—Gene Mancene
Assistant Examiner—John J. Wilson
Attorney, Agent, or Firm—Townsend & Townsend

[57] ABSTRACT

A dental implant having a core member formed of a gingiva-compatible metal for mounting a dental superstructure in the shape of a tooth crown; a fastening element for dental bridges or the like, wherein the core member is connected with a tissue-compatible biostable polymer matrix which contains reabsorbable, bioreactive sintered calcium phosphate. The core member is constructed from a metal plate flat in cross-section and conformed with the implant shape and which is provided with apertures, wherein the polymer matrix is a covering encompassing the metal plate on all sides thereof and is constituted of a biostable polymer material and reabsorbable finely-divided, sintered calcium phosphate, and in which the apertures are filled with reabsorbable sintered calcium phosphate.

6 Claims, 6 Drawing Figures

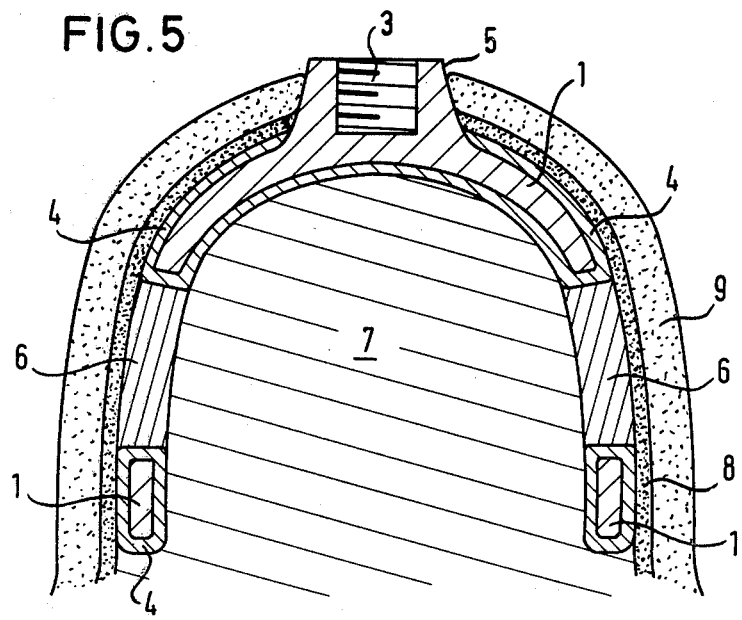
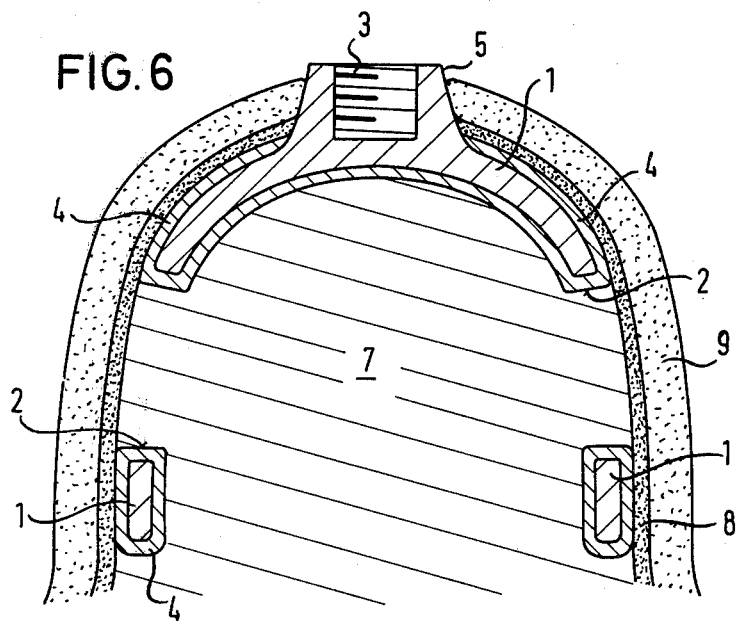

DENTAL IMPLANT

BACKGROUND OF THE INVENTION

1. Field of the Invention

The present invention relates to a dental implant having a core member formed of a gingiva-compatible metal for mounting a dental superstructure in the shape of a tooth crown; a fastening element for dental bridges or the like, wherein the core member is connected with a tissue-compatible biostable polymer matrix which contains reabsorbable, bioreactive sintered calcium phosphate.

2. Discussion of the Prior Art

Heretofore known and primarily employed implants consist of an anchoring component of metal and are shaped in the form of a plate, needle, screw or the like, and are based on a purely mechanical interengagement with the bone so as to achieve an anchoring of the prosthesis on the bone. In the interim it has been recognized that a plurality of technological material requirements must be fulfilled concurrently in order to be able to attain a permanent stable implantation. The utilized materials must be biocompatible with the bone and the configuration of the implant and the mechanical properties of the materials must provide a physiologically correct load and force distribution since, otherwise, the bone will react through deterioration and finally through loosening of the implant.

The shape of the implant and the instrumentability for its implanting must allow for a simple implanting which is correlated with the current conditions. The implant must in all areas provide for a direct, permanent and bone-like connection with the jaw and cannot be encapsulated with regard to the bone by a connective tissue membrane.

For this purpose, more recently there have become known bioactive materials which effect a connective tissue-free growing together of the bone with the material surface of the anchoring component. Such materials, for example, deal with calcium phosphate of a predetermined composition in which there occurs a direct connective tissue-free growing together of the bone with the material (Köster, "Experimenteller Knochenersatz durch resorbierbare Calciumphosphatkeramik", Langenbecks Archiv für Chirogie 341, 77–86 (1976)). These calcium phosphates are decomposable in a biological milieu, meaning they are absorbed by the cells which are active during bone formation and thus fulfill the set basic biochemical requirement, nevertheless they do not come into consideration as the exclusive material for a permanently implanted prosthesis due to the lack of a permanent anchoring between the material of the anchoring component and the bone.

In order to produce a permanent anchoring of implants subject to high loads, in which there is achieved a really permanent connection between the prosthesis and the tissue, it has become known to formulate the prosthesis anchoring as a coating on the prosthesis shank, and to so embed the ceramic calcium phosphate having a particulate form of predetermined particle diameter size in the plastic material that, during the reabsorption of the ceramic component there is produced a matrix of plastic material which is porous throughout, and on whose inner pore surfaces there will remain bioactive residues of the ceramic.

In accordance with another proposal for an implantable tooth root, this consists essentially of a biostable polymer matrix which is compatible with human cell tissue, in which there is embedded the reabsorbable bioreactive calcium phosphate in a finely dispersed form, which is encompassed by a thin porous layer of non-reabsorbable calcium phosphate, and into which there is inserted a core as a connecting member for the mounting of a dental superstructure. Extraordinarily good results have been achieved with implants of that type, however, they are relatively complex, particularly with respect to the production of the polymer matrix with embedded calcium phosphate particles of predetermined construction.

SUMMARY OF THE INVENTION

Accordingly, it is an object of the present invention to provide a simply produced dental implant which facilitates for an improved and stable connective tissue-free growing thereof into the jawbone.

A more specific object lies in the provision of a dental implant of the above-mentioned type which is characterized in that the core member is constructed from a metal plate flat in cross-section and conformed with the implant shape and which is provided with apertures, wherein the polymer matrix is a covering encompassing the metal plate on all sides thereof and is constituted of a biostable polymer material and reabsorbable finely-divided, sintered calcium phosphate, and in which the apertures are filled with reabsorbable sintered calcium phosphate.

Achieved thereby are the following advantages: The construction of the core member as a metal plate which is flat in cross-section and which is conformed to the implant configuration, in a suitable embodiment for example, is constructed either saddle-shaped or tubularly-shaped, and permits a two-sided growing in of the bone tissue. The reabsorbable calcium phosphate which is introduced into the apertures provided herein is fully reabsorbed by the bone tissue so as to result in a growing of the bone tissue through the core member, and to thusly provide a stable penetrating growing together of the bone with the implant. The polymer matrix which is formed as a coating creates a tissue-compatible anchoring capability for all areas of the core member which comes into contact with the bone, whereby the bone tissue will reabsorb only a portion of the calcium phosphate in the plastic material coating and the remainder of the not reabsorbed calcium phosphate will create a connective tissueless band with the bone. Hereby, no large demands are made in the production of the coating of biostable plastic material and reabsorbable calcium phosphate, particularly with respect to the particle configuration of the calcium phosphate, since for the stable growing in of the newly formed bone tissue with the reabsorbing of the calcium phosphate, there is created an especially large surface, and the mechanically stable connection between the implant and the bone is essentially formed by the growth of bone tissue through the apertures under the reabsorption of the calcium phosphate.

In the construction of the core member as a saddle-shaped metal plate provided with apertures, the bone tissue can grow from the interior outwardly through the apertures toward the bone membrane (periost) which has been removed prior to the insertion of the saddle implant, and from outwardly when again reapplied subsequent to the fitting of the implant on the bone. This will then produce an intimate bond and also the bone membrane (periost) finds a tissue-compatible milieu in the form of the coating which is provided on all sides of the core member so as to facilitate its ingrowth.

In the construction of the core member as a tubularly-shaped metal plate which is provided with apertures, under the reabsorption of the calcium phosphate which is present in the apertures there is effected an intimate growing together of the bone with the inner bone tenon which will remain after formation of the tubularly-shaped milled location in the bone for the insertion of the tubularly-shaped implant. When this bone tenon cannot be obtained as a result of the low extent of bone tissue, then not only the apertures in the implant but also the entire interior region of the tubularly-shaped core member can be filled with reabsorbable calcium phosphate.

In a preferred embodiment of the invention, the metal plate which forms the core member is constituted of titanium, and the coating of approximately 20% to 30% polymethylmethacrylate (PMMA) and about 70% to 80% of sintered, ground into powder and finely dispersed distributed tricalcium phosphate. Since, as mentioned with respect to the production of the coating in contrast with heretofore known polymer matrixes, not such high requirements are set with regard to size and distribution of the calcium phosphate particles, the coating can be inventively applied in a simple manner on the metal plate forming the core member by dipping, spraying, painting or the like. Thereby, the surface of the metal plate must previously be well cleaned either by sand-blasting or the like, and provided with an adhesive medium.

In a further advantageous embodiment of the invention, the reabsorbable, sintered calcium phosphate can be prepared in the shape of tablets corresponding in size to the apertures and inserted in the apertures. In addition thereto, the quantity and size of the apertures can be varied according to need in view of mechanical stability which is to be attained and the condition of the available bone tissue. Just as well, in addition to the mentioned saddle-shaped and tubularly-shaped implant configurations, it is also possible to contemplate other suitable configurations for the metal plate which is flat in cross-section, and which will facilitate a two-sided growing in and through of the bone tissue through the apertures.

BRIEF DESCRIPTION OF THE DRAWINGS

Reference may now be had to the following description of exemplary embodiments of the invention, taken in conjunction with the accompanying drawings; in which:

FIG. 5 illustrates, in an enlarged scale, a section through an inserted saddle implant prior to the reabsorption of the calcium phosphate components; and FIG. 6 is a sectional view similar to that of FIG. 5 showing the implant after the reabsorption of the calcium phosphate components.

DETAILED DESCRIPTION

Figure 1:
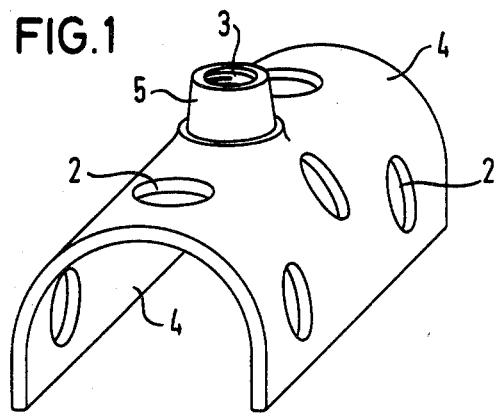
FIG. 1 schematically illustrates, in a perspective view, a saddle-shaped implant constructed pursuant to the invention.
Figure 2:
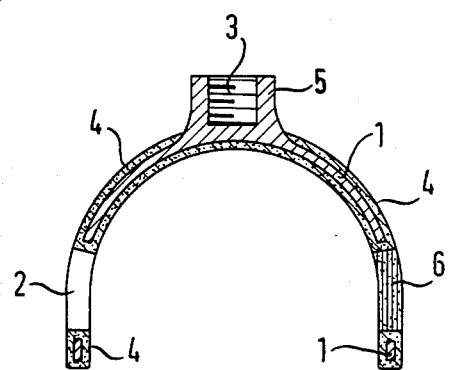
FIG. 2 is a transverse cross-section through the implant shown in FIG. 1.

The implant illustrated in FIGS. 1 and 2 of the drawings is constructed saddle-shaped and consists of a metal plate 1 of tissue-compatible metal, preferably titanium, which includes apertures 2. The metal plate 1 includes at its upper surface a threaded headpiece 3 for the receipt of the connecting elements of dental superstructures, such as crowns, bridges or the like. The metal plate, on all sides thereof inclusive of the edges of the apertures 2, is encompassed by a coating 4 of a biostable polymer plastic material having reabsorbable calcium phosphate embedded therein whereby merely the outer surface 5 of the threaded headpiece 3 is free of the cover 4 so as to facilitate a tight contact of the gingiva (gum skin); compare FIGS. 5 and 6. The apertures 2 are filled with reabsorbable sintered tricalcium phosphate 6 whereby, for reasons of clarity, in FIG. 2 only the right side shows the calcium phosphate ceramic 6. This can be prepared in tablet form and inserted in the apertures 2.

Figure 3:
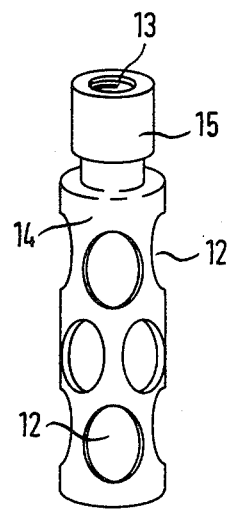
FIG. 3 schematically illustrates, in a perspective view, a tubularly-shaped pin implant.
Figure 4:
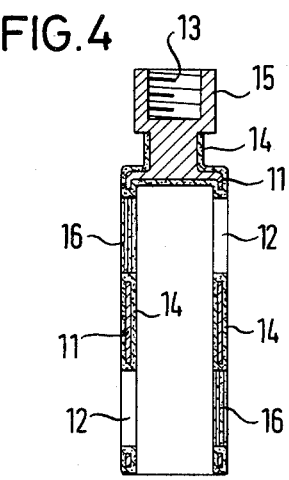
FIG. 4 is a longitudinal section through the implant of FIG. 3.

In the embodiment according to FIGS. 3 and 4, the metal plate 11 forming the core member is tubularly constructed, having an open end and a closed end supporting a threaded headpiece 13 for the fastening of the superstructure. The apertures in the metal plate 11 are designated by reference numeral 12, whereas the calcium phosphate inserted in these apertures, upon occasion prepared in tablet shape, is designated by reference numeral 16 and shown in FIG. 4 merely at two locations. The coating which encompasses the metal plate 11 on all sides thereof is designated by reference numeral 14, the free polished surface for the tissue-compatible application of the gingiva on the threaded head 13 is designated by reference numeral 15.

In the saddle implant illustrated in a sectional view in FIGS. 5 and 6, the portions of the implant which correspond to the embodiment of FIGS. 1 and 2 are designated with the same reference numerals and are not again elucidated. The jawbone is designated by reference numeral 7, the periost (bone membrane) with reference numeral 8, and the gingiva (gum skin) with reference numeral 9. For carrying out of the implanting, the gingiva 9 is pulled back and the periost is peeled off carefully while being similarly folded away. After the milling prepping of the jawbone 7 there is carried out the insertion of the implant and the application of periost 8 and the gingiva 9. This condition is illustrated in FIG. 5 of the drawings. The bone 7, as well as the periost 8 are located exclusively on a tissue-compatible, at least partially reabsorbable and a connective tissue-free growth-permitting surface of the coating 4, in essence the calcium phosphate ceramic 6 in the apertures 2. After the reabsorption of the calcium phosphate 6 and the growing through of the newly formed bone tissue there is obtained the condition shown in FIG. 6. An intimate bond is indicated between newly formed bone tissue 7 in the apertures 2 and the periost 8. Not shown herein is the partial reabsorption of the calcium phosphate in the covering 4 and the connective tissue-free growth of the bone tissue into the coating 4.

What is claimed is:

1. In a dental implant including a gingiva-compatible metal core member for mounting a dental superstructure in the form of a tooth crown, a fastening element for dental bridges or the like in which the member is connected with a tissue-compatible, biostable polymer matrix having reabsorbable, bioreactive, sintered calcium phosphate, the improvement comprising: said core member being a flat metal plate (1, 11) conformed in shape to said implant and being provided with through-apertures (2, 12) and the polymer matrix is a coating (4, 14) encompassing the metal plate (1, 11) on all sides thereof, and said through-apertures (2, 12) are filled with reabsorbable, sintered calcium phosphate (6, 16).

2. Implant as claimed in claim 1, said apertured metal plate having a saddle-shaped configuration; and means on the upper surface of said metal plate extending through said coating for the mounting and fastening of the dental superstructure.

3. Implant as claimed in claim 1, said apertured metal plate being tubularly shaped and having an upper closed end; means on the upper closed end of said metal plate extending through said coating for the mounting and fastening of the dental superstructure.

4. Implant as claimed in claim 1, said metal plate being constituted of titanium, and said coating being constituted of about 20% to 30% polymethylmethacrylate (PMMA) and about 70% to 80% of powder ground, sintered and finely dispersedly distributed tricalcium phosphate.

5. Implant as claimed in claim 4, the surface of said metal plate being cleaned by sandblasting and provided with an adhesive medium, said coating being applied to said surface through dipping, spraying, painting or the like.

6. Implant as claimed in claim 1, said reabsorbable sintered calcium phosphate being prepared in tablets corresponding in size to said apertures and being positioned within said apertures.

* * * * *